US008653110B2

(12) United States Patent
Kilian et al.

(10) Patent No.: US 8,653,110 B2
(45) Date of Patent: Feb. 18, 2014

(54) ACTIVE COMPOUND COMBINATION COMPRISING AZADIRACHTIN AND A SUBSTITUTED ENAMINOCARBONYL COMPOUND

(75) Inventors: Michael Kilian, Leverkusen (DE); Margit Doth, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 244 days.

(21) Appl. No.: 13/020,960

(22) Filed: Feb. 4, 2011

(65) Prior Publication Data

US 2011/0207778 A1 Aug. 25, 2011

Related U.S. Application Data

(60) Provisional application No. 61/301,755, filed on Feb. 5, 2010.

(30) Foreign Application Priority Data

Feb. 5, 2010 (EP) .................................... 10152723

(51) Int. Cl.
| | | |
|---|---|---|
| *A01N 25/00* | (2006.01) | |
| *A01N 43/40* | (2006.01) | |
| *A61K 31/44* | (2006.01) | |
| *A01N 43/08* | (2006.01) | |
| *A61K 31/34* | (2006.01) | |
| *C07D 405/00* | (2006.01) | |
| *C07D 211/72* | (2006.01) | |
| *C07D 211/84* | (2006.01) | |

(52) U.S. Cl.
USPC ........ 514/336; 514/473; 424/405; 546/284.4; 546/345

(58) Field of Classification Search
USPC ......... 514/336, 473; 546/284.4, 345; 424/405
See application file for complete search history.

(56) References Cited

U.S. PATENT DOCUMENTS

| 4,245,432 | A | 1/1981 | Dannelly |
|---|---|---|---|
| 4,272,417 | A | 6/1981 | Barke et al. |
| 4,808,430 | A | 2/1989 | Kouno |
| 5,876,739 | A | 3/1999 | Turnblad et al. |
| 8,084,452 | B2 * | 12/2011 | Jeschke et al. ................. 514/247 |
| 8,106,211 | B2 * | 1/2012 | Jeschke et al. ............. 546/279.7 |
| 2003/0176428 | A1 | 9/2003 | Schneidersmann et al. |
| 2009/0253749 | A1 | 10/2009 | Jeschke et al. |
| 2010/0197494 | A1 | 8/2010 | Hungenberg et al. |
| 2010/0204048 | A1 | 8/2010 | Hungenberg et al. |

FOREIGN PATENT DOCUMENTS

| EP | 0 539 588 A1 | 5/1993 |
|---|---|---|
| EP | 0 834 254 A1 | 4/1998 |
| WO | WO 02/28186 A2 | 4/2002 |
| WO | WO 02/080675 A1 | 10/2002 |
| WO | WO 2007/115644 A1 | 10/2007 |
| WO | WO 2009/043438 A1 | 4/2009 |

OTHER PUBLICATIONS

Bauer, T.A., et al., "Response of Selected Weed Species to Postemergence Imazethapyr and Bentazon," *Weed Tech. 9*: 236-242, The Weed Science Society of America (1995).
Blackshaw, R.E., "HOE-39866 Use in Chemical Fallow Systems," *Weed Tech. 3*:420-428, The Weed Science Society of America (1989).
Blackshaw, R.E., "Synergistic Mixes of DPX-A7881 and Clopyralid in Canola (*Brassica napus*)," *Weed Tech. 3*:690-695, The Weed Science Society of America (1989).
Blackshaw, R.E., et al., "Herbicide Combinations for Postemergent Weed Control in Safflower (*Carthamus tinctorius*)," *Weed Tech. 4*:97-104, The Weed Science Society of America (1990).
Blouin, D.C., et al., "Analysis of Synergistic and Antagonistic Effects of Herbicides Using Nonlinear Mixed-Model Methodology," *Weed Tech. 18*:464-472, The Weed Science Society of America (2004).
Bradley, P.R., et al., "Response of Sorghum (*Sorghum bicolor*) to Atrazine, Ammonium Sulfate, and Glyphosate," *Weed Tech. 14*:15-18, The Weed Science Society of America (2000).
Buker, III, R.S., et al., "Confirmation and Control of a Paraquat-Tolerant Goosegrass (*Eleusine indica*) Biotype," *Weed Tech. 16*:309-313, The Weed Science Society of America (2002).
Burke, I.C., et al., "CGA-362622 Antagonizes Annual Grass Control with Clethodim," *Weed Tech. 16*:749-754, The Weed Science Society of America (2002).
Colby, S.R., "Calculating Synergistic and Antagonistic Responses of Herbicide Combinations," *Weeds 15*: 20-22, Weed Society of America (1967).
Flint, J.L., et al., "Analyzing Herbicide Interactions: A Statistical Treatment of Colby's Method," *Weed Tech. 2*:304-309, The Weed Science Society of America (1988).
Gillespie, G.R., and Nalewaja, J.D., "Wheat (*Triticum aestivam*) Response to Triallate Plus Chlorsulfuron," *Weed Tech. 3*:20-23, The Weed Science Society of America (1989).
Green, J.M., et al., "Metribuzin and Chlorimuron Mixtures for Preemergence Broadleaf Weed Control in Soybeans, Glycine max," *Weed Tech. 2*:355-363, The Weed Science Society of America (1988).
Harker, K.N., and O'Sullivan, P.A., "Synergistic Mixtures of Sethoxydim and Fluazifop on Annual Grass Weeds," *Weed Tech. 5*:310-316, The Weed Science Society of America (1991).
Kent, L.M., et al., "Effect of Ammonium Sulfate, Imazapyr, and Environment on the Phytotoxicity of Imazethapyr," *Weed Tech. 5*:202-205, The Weed Science Society of America (1991).
Kotoula-Syka, E., et al., "Interactions between SAN 582H and Selected Safeners on Grain Sorghum (*Sorghum bicolor*) and Corn (*Zea mays*)," *Weed Tech. 10*:299-304, The Weed Science Society of America (1996).
Lanclos, D.Y., et al., "Glufosianate Tank-Mix Combinations in Glufosinate-Resistant Rice (*Oryza sativa*)," *Weed Tech. 16*:659-663, The Weed Science Society of America (2002).

(Continued)

*Primary Examiner* — Kara R McMillian
(74) *Attorney, Agent, or Firm* — Sterne, Kessler, Goldstein & Fox P.L.L.C.

(57) ABSTRACT

Disclosed are novel active compound combinations comprising at least one substituted enaminocarbonyl compound and azadirachtin, which combinations are highly suitable for controlling animal pests such as insects and unwanted acarids. Methods of controlling insects and acarids are also disclosed.

14 Claims, No Drawings

(56) References Cited

OTHER PUBLICATIONS

Norris, J.L., et al., "Weed Control from Herbicide Combinations with Three Formulations of Glyphosate," *Weed Tech. 15*:552-558, The Weed Science Society of America (2001).

Novosel, K.M., et al., "Metolachlor Efficacy as Influenced by Three Acetolactate Synthase-Inhibiting Herbicides," *Weed Tech. 12*:248-253, The Weed Science Society of America (1998).

Palmer, E.W., et al., "Broadleaf Weed Control in Soybean (*Glycine max*) with CGA-277476 and Four Postemergence Herbicides," *Weed Tech. 14*:617-623, The Weed Science Society of America (2000).

Rummens, F.H.A., "An Improved Definition of Synergistic and Antagonistic Effects,"*Weed Science 23*(1):4-6, The Weed Science Society of America, United States (1975).

Salzman, F.P., and Renner, K.A., "Response of Soybean to Combinations of Clomazone, Metribuzin, Linuron, Alachlor, and Atrazine," *Weed Tech. 6*:922-929, The Weed Science of America (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim,"*Weed Tech. 12*:463-469, The Weed Science Society of America (1998).

Shaw, D.R. and Arnold, J.C., "Weed Control from Herbicide Combinations with Glyphosate," *Weed Tech. 16*:1-6, The Weed Science Society of America (2002).

Snipes, C.E., and Allen, R.L., "Interaction of Graminicides Applied in Combination with Pyrithiobac," *Weed Tech. 10*:889-892, The Weed Science Society of America (1996).

Sun, Y.-P. & Johnson, E.R., "Analysis of Joint Action of Insecticides Against House Files", *J. Econ. Entomol. 53*:887-892, United States (1960).

Tammes, P.M.L., "Isoboles, A Graphic Representation of Synergism in Pesticides," *Neth. J. Plant Path. 70*:73-80, Springer, Germany (1964).

Wehtje, G. and Walker, R.H., "Interaction of Glyphosate and 2,4-DB for the Control of Selected Morningglory (*Ipomoea* spp.) Species," *Weed Tech. 11*:152-156, The Weed Science Society of America (1997).

Zhang, W., et al., "Fenoxaprop Interactions for Barnyardgrass (*Echinochloa crus-galli*) Control in Rice," *Weed Tech. 19*:293-297, The Weed Science Society of America (2005).

International Search Report for International Application No. PCT/EP2011/051577, European Patent Office, Netherlands, mailed Aug. 31, 2011.

Office Action for U.S. Appl. No. 12/295,458, § 371(c) Date: Jan. 24, 2009, inventors Jeschke, P. et al., U.S. Patent and Trademark Office, Alexandria, Virginia, mailed Oct. 8, 2010.

Office Action for U.S. Appl. No. 12/295,355, § 371(c) Date: Mar. 11, 2009, inventors Jeschke, P. et al., U.S. Patent and Trademark Office, Alexandria, Virginia, mailed Apr. 18, 2011.

\* cited by examiner

ACTIVE COMPOUND COMBINATION COMPRISING AZADIRACHTIN AND A SUBSTITUTED ENAMINOCARBONYL COMPOUND

FIELD OF THE INVENTION

The present invention relates to novel active compound combinations comprising at least one particular substituted enaminocarbonyl compound and azadirachtin, which combinations are highly suitable for controlling animal pests such as insects and unwanted acarids.

The invention also relates to methods for controlling animal pests on plants and seed, to the use of the active compound combinations according to the invention for treating seed, to a method for protecting seed and not least to the seed treated with the active compound combinations according to the invention.

BACKGROUND OF THE INVENTION

It is already known from EP-A-0 539 588 and WO 2007/115644 to use substituted enaminocarbonyl compounds as crop protection agents for controlling insects and acarids. It is also known to use substituted enaminocarbonyl compounds together with other insecticides. Thus, for example, WO 2009/043443 describes active compound combinations comprising certain substituted enaminocarbonyl compounds and certain neonicotinoid insecticides, such as, for example, clothianidin or thiamethoxam.

It is also already known that the extracts of the seeds of the neem tree have insecticidal properties (cf. "Römpp Chemie Lexikon", 9th edition, page 2954, Georg Thieme Verlag, Stuttgart-New York, 1991). The activity of the neem tree extract is generally ascribed to the presence of azadirachtin. Azadirachtin belongs to the limonoids and is a secondary metabolite. Azadirachtin is a highly oxidized tetranortriterpenoid having enol ether, acetal, hemiacetal and epoxide functions. Azadirachtin has in particular ecdysone-like activity, i.e. it inhibits the larval development of various insects (Z. Naturforsch., part C, 42, 4 (1987)). Azadirachtin has the disadvantage that the onset of this activity of the active compound is delayed, and that, at low application rates, the efficacy is sometimes unsatisfactory.

In general, the activity of the known substituted enaminocarbonyl compounds and of azadirachtin is good. However, in particular at low application rates and in the case of certain pests, they do not always satisfy the requirements of agricultural and horticultural practice, and there is still a need for an economically efficient and ecologically safe pest control.

However, since the ecological and economical demands made on modern crop protection agents are increasing constantly, for example with respect to toxicity, selectivity, application rate, formation of residues and favourable manufacture, and there can furthermore be problems, for example, with resistances, there is a constant need to develop novel crop protection agents which, at least in some areas, have advantages over the known ones.

Accordingly, it is an object of the present invention to provide further insecticides which, compared to known active compound combinations, have an improved activity and/or a broader activity spectrum and avoid the disadvantages mentioned above.

SUMMARY OF THE INVENTION

We have now found that a combination of certain substituted enaminocarbonyl compounds with the active compound azadirachtin present in the extract of the seeds of the neem tree has, in addition to a synergistic increase of activity, a broader activity spectrum. It has also been found that the active compound combination according to the invention accelerates the action profile of the azadirachtin. Furthermore, an improved duration of action may be observed. Accordingly, the invention relates to an active compound combination comprising at least one substituted enaminocarbonyl compound of the formula (I-1), (I-2) or (I-3) and azadirachtin. Here, azadirachtin may be present in the form of the pure active compound or as a formulation comprising azadirachtin or in the form of the extract of the seeds of the neem tree and their formulations.

DETAILED DESCRIPTION OF THE INVENTION

The substituted enaminocarbonyl compounds according to the invention are 4-{[(6-chloropyrid-3-yl)methyl](2,2-difluoroethyl)amino}furan-2(5H)-one (compound (I-1)), the insecticidal action of which was described for the first time in WO 2007/115644; 4-{[(6-chloropyrid-3-yl)methyl](cyclopropyl)amino}furan-2(5H)-one (compound (I-2)) and 4-{[(6-chloropyrid-3-yl)methyl](methyl)amino}furan-2 (5H)-one (compound (1-3)), the insecticidal activity of which was described for the first time in EP-A-0 539 588. The compounds can be prepared by the processes described in WO2007/115644 and EP-A-0539588 and have the following structures:

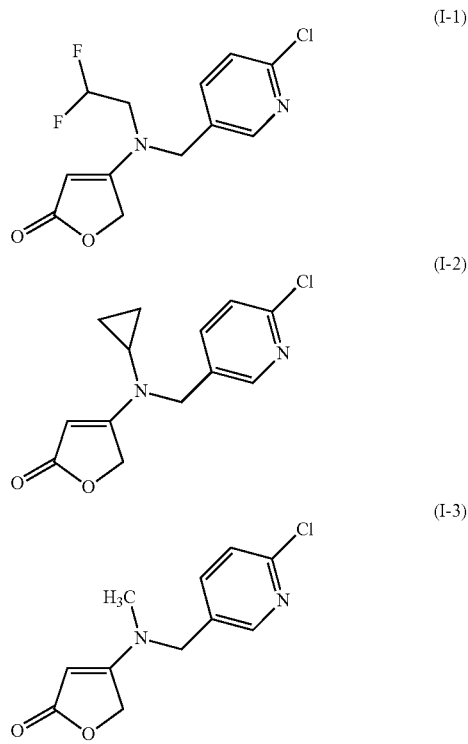

In addition to the activity described above, the active compound combinations according to the invention may show further surprising advantages, including increased safety in use; reduced phytotoxicity and thus better tolerance by plants; the control of pests in their different development stages; better behaviour during production of the insecticidal compounds, for example during grinding or mixing, during their storage or during their use; a very advantageous biocidal spectrum, even at low rates of concentration, while being well tolerated by warm-blooded organisms, fish and plants; and achievement of an additional effect, for example an algicidal, anthelmintic, avicidal, bactericidal, fungicidal, molluscicidal, nematicidal, plant-activating, rodenticidal or virucidal action.

It was further found that the active compound combinations according to the invention are particularly suited for the protection of seed and/or shoots and foliage of a plant grown from the seed from damage by pests. Thus, the active compound combinations according to the invention show negligible phytotoxicity when applied to the plant propagation material, compatibility with soil conditions (e.g. concerning binding of the compound to the soil), systemic activity in the plant, no negative impact on germination, and efficacy during appropriate pest life cycle.

In one embodiment, the invention relates to an active compound combination which essentially consists of 4-{[(6-chloropyrid-3-yl)methyl](2,2-difluoroethyl)amino}furan-2(5H)-one (compound (I-1)) and azadirachtin, preferably in a ratio which accelerates the action of azadirachtin.

In a further embodiment, the invention relates to an active compound combination which essentially consists of 4-{[(6-chloropyrid-3-yl)methyl](cyclopropyl)amino}furan-2(5H)-one (compound (I-2)) and azadirachtin, preferably in a ratio which accelerates the action of azadirachtin.

In yet a further embodiment, the invention relates to an active compound combination which essentially consists of 4-{[(6-chloropyrid-3-yl)methyl](methyl)amino}furan-2(5H)-one (compound (1-3)) and azadirachtin, preferably in a ratio which accelerates the action of azadirachtin.

According to the invention, the active compound combination according to the invention preferably comprises one of the compounds of the formula (I-1), (I-2) or (I-3) and azadirachtin in a mixing ratio in the range of from about 125:1 to about 1:125, particularly preferably in the range of from about 25:1 to about 1:25, very particularly preferably in the range of from about 5:1 to about 1:5.

The compounds of the formula (I-1), (I-2) or (I-3) having at least one basic centre are capable of forming, for example, acid addition salts, for example with strong inorganic acids such as mineral acids, for example perchloric acid, sulphuric acid, nitric acid, nitrous acid, a phosphorus acid or a hydrohalic acid, with strong organic carboxylic acids such as unsubstituted or substituted, for example halogen-substituted, $C_1$-$C_4$-alkanecarboxylic acids, for example acetic acid, saturated or unsaturated dicarboxylic acids, for example oxalic acid, malonic acid, succinic acid, maleic acid, fumaric acid and phthalic acid, hydroxycarboxylic acids, for example ascorbic acid, lactic acid, malic acid, tartaric acid and citric acid, or benzoic acid, or with organic sulphonic acids such as unsubstituted or substituted, for example halogen-substituted, $C_1$-$C_4$-alkane- or arylsulphonic acids, for example methane- or p-toluenesulphonic acid. The compounds of the formula (I-1), (I-2) or (I-3) having at least one acidic group are capable of forming, for example, salts with bases, for example metal salts, such as alkali or alkaline-earth metal salts, for example sodium, potassium or magnesium salts, or salts with ammonia or an organic amine such as morpholine, piperidine, pyrrolidine, a lower mono-, di- or trialkylamine, for example, ethyl-, diethyl-, triethyl- or dimethylpropylamine, or a lower mono-, di- or trihydroxyalkylamine, for example mono-, di- or triethanolamine. Moreover, if appropriate, it may also be possible for corresponding internal salts to be formed. In the context of the invention, agrochemically advantageous salts are preferred. Taking into consideration the close relationship between the compounds of the formula (I-1), (I-2) or (I-3) in free form and in the form of their salts, any reference hereinabove and hereinbelow to the free compounds of the formula (I-1), (I-2) or (I-3) or to their salts is to be interpreted such that, if appropriate and expedient, the corresponding salts or the free compounds, respectively, of the formula (I-1), (I-2) or (I-3) are also included. This also applies correspondingly to tautomers of the compounds of the formula (I-1), (I-2) or (I-3) which are possible and to their salts.

In the present case, extracts of seeds of the neem tree are to be understood as meaning all customary products which can be isolated from seeds of the neem tree by extraction or pressing and which comprise substantial amounts of azadirachtin. The extraction process also yields byproducts which also comprise azadirachtin, such as, for example, neem oil or the solid residual cake which essentially comprises the solid components of the neem seeds and is frequently used as fertilizer. The extraction product comprises the various azadirachtin isomers A to K, but mainly azadirachtin A. In the context of the present invention, azadirachtin-comprising products are to be understood as meaning not only the extraction product itself but also the byproducts. Here, both the extraction products and the byproducts can be present in formulations, which can likewise be employed according to the invention. The proportion of azadirachtin A (molecular weight 720.7 g/mol) serves to characterize the commercial products. The proportion of the isomers may be determined by HPLC. Preference is given to using products having a proportion of from 20% to 50%, preferably from 25% to 40%, particularly preferably from 30% to 40%, of azadirachtin A. Particular preference is given to NeemAzal® technical from Trifolio-M GmbH.

Azadirachtin may also be provided in the form of a pure active compound, e.g., one or more of the various azadirachtin isomers A to K, including azadirachtin A. By the term "pure active compound" is meant the said one or more azadirachtin isomers A-K substantially free of other substances, e.g., said extraction byproducts, for example, neem oil or the solid residual cake which essentially comprises the solid components of the neem seeds and is frequently used as a fertilizer.

By the term "substantially free" is meant the one or more azadirachtin isomers A-K comprises less than about 40% of other substances, e.g., the said extraction byproducts, as established using conventional analytical methods routinely used by those of skill in the art. In some embodiments, the amount of other substances is less than about 35%, or less than about 30%, or less than about 25%, or less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5%.

In the context of the present invention, the term "active compound combination" refers to various combinations of compounds of the formula (I-1), (I-2) or (I-3) and azadirachtin, for example in the form of a single ready-mix, in a combined spray mixture composed of separate formulations of the individual active compounds, for example a tank-mix or in a combined use of the individual active compounds in the case of their sequential application, for example in succession within an appropriate short period of time of, for example, a few hours or days. According to a preferred embodiment, the order of the application of the compounds of the formula (I-1), (I-2) or (I-3) and azadirachtin is not critical for the practice of the present invention.

When using the active compound combinations according to the invention as insecticides and acaricides, the application rates can be varied within a relatively wide range, depending on the kind of application. The application rate of the active compound combinations according to the invention is when treating plant parts, e.g. leaves, and pests, from 0.1 to 10 000 g/ha, preferably from 10 to 1000 g/ha, particularly preferably from 50 to 300 g/ha (when the application is carried out by watering or dripping, it may even be possible to reduce the application rate, in particular when inert substrates such as rock wool or perlite are used); when treating seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed; when treating the soil: from 0.1 to 10 000 g/ha, preferably from 1 to 5000 g/ha.

The active compound combinations according to the invention can be used to protect plants for a certain period of time after the treatment against attack by the animal pests mentioned. The period for which protection is provided extends generally for 1 to 42 days, preferably for 1 to 28 days, particularly preferably for 1 to 14 days after the treatment of the plants and/or pests with the active compounds, or for up to 200 days after a seed treatment.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and also against all or some stages of development. The abovementioned pests include:

From the phylum Mollusca, for example from the class of the Lamellibranchiata, for example *Dreissena* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the phylum Arthropoda, for example from the order of the Isopoda, for example *Armadillidium vulgare, Oniscus asellus, Porcellio scaber.*

From the class of the Arachnida, for example, *Acarus* spp., *Aceria sheldoni, Aculops* spp., *Aculus* spp., *Amblyomma* spp., Amphi*tetranychus viennensis,* Argas spp., *Boophilus* spp., *Brevipalpus* spp., *Bryobia praetiosa,* Centruroides spp., *Chorioptes* spp., *Dermanyssus gallinae, Dermatophagoides pteronyssius, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici.*

From the order of the Symphyla, for example, *Scutigerella* spp.

From the order of the Chilopoda, for example, *Geophilus* spp., *Scutigera* spp.

From the order of the Collembola, for example, *Onychiurus armatus.*

From the order of the Diplopoda, for example, *Blaniulus guttulatus.*

From the order of the Zygentoma, for example, *Lepisma saccharina, Thermobia domestica.*

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

From the order of the Isoptera, for example, *Coptotermes* spp., *Cornitermes cumulans, Cryptotermes* spp., *Incisitermes* spp., *Microtermes obeli, Odontotermes* spp., *Reticulitermes* spp.

From the order of the Heteroptera, for example, *Anasa tristis, Antestiopsis* spp., *Boisea* spp., *Blissus* spp., *Calocoris* spp., *Campylomma livida, Cavelerius* spp., *Cimex lectularius, Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Anoplura (Phthiraptera), for example, *Damalinia* spp., *Haematopinus* spp., *Linognathus* spp., *Pediculus* spp., *Ptirus pubis, Trichodectes* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pin, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Sticto-*

*cephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Coleoptera, for example, *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum, Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Hymenoptera, for example, *Acromyrmex* spp., *Athalia* spp., *Atta* spp., *Diprion* spp., *Hoplocampa* spp., *Lasius* spp., *Monomorium pharaonis, Solenopsis invicta, Tapinoma* spp., *Vespa* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp., *Lucilia* spp., *Lutzomia* spp., *Mansonia* spp., *Musca* spp., *Nezara* spp., *Oestrus* spp., *Oscinella frit, Pegomyia* spp., *Phlebotomus* spp., *Phorbia* spp., *Phoimia* spp., *Prodiplosis* spp., *Psila rosae, Rhagoletis* spp., *Sarcophaga* spp., *Simulium* spp, *Stomoxys* spp., *Tabanus* spp., *Tannia* spp., *Tetanops* spp., *Tipula* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Siphonaptera, for example, *Ceratophyllus* spp., *Ctenocephalides* spp., *Tunga penetrans, Xenopsylla cheopis.*

From the phyla of the Plathelminths and Nematodes as animal parasites, for example from the class of the Helminths, for example *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

From the phylum of the Nematodes as plant pests, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

From the subphylum of the Protozoa, for example *Eimeria.*

If appropriate, the active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms).

The present invention furthermore relates to formulations and use forms prepared therefrom (crop protection compositions or pesticides) comprising the active compound combination according to the invention. These are preferably insecticidal formulations or use forms comprising auxiliaries such as, for example, extenders, solvents, carriers and/or other auxiliaries such as, for example, surfactants.

To prepare the formulations, the extracts of seeds of the neem tree are used as a commercial preparation or in the form of the isolated substance.

Customary formulations are, for example, solutions, emulsions, wettable powders, water- and oil-based suspensions, water- and oil-based suspension concentrates, powders, dusts, pastes, soluble powders, foams, granules, dispersible granules, soluble granules, granules for broadcasting, suspoemulsion concentrates, natural compounds impregnated with active compound, synthetic substances impregnated with active compound, fertilizers and also microencapsulations in polymeric substances.

These formulations are prepared in a known manner, for example by mixing the active compounds with auxiliaries such as, for example, extenders, solvents and/or solid carriers and/or further auxiliaries such as, for example, surfactants. The formulations are prepared either in suitable facilities or else before or during application.

Auxiliaries used may be substances capable of giving the formulation of the active compound, or the application forms prepared from these formulations (such as ready-to-use crop protection compositions, for example, such as spray liquors or seed dressings) particular properties, such as certain physical, technical and/or biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle it is possible to use all suitable carriers. Suitable carriers are: for example ammonium salts and ground natural minerals such as kaolins, clays, talc, chalk, quartz, attapulgite, montmorillonite or diatomaceous earth, and ground synthetic materials such as finely divided silica, alumina and natural and synthetic silicates, resins, waxes and/or solid fertilizers. Mixtures of such carriers may also be used. Suitable carriers for granules are: for example crushed and fractionated natural minerals such as bentonite, calcite, marble, pumice, sepiolite, dolomite, kaolinite, and also synthetic granules of inorganic and organic meals, and also granules of organic material such as sawdust, paper, coconut shells, maize cobs and tobacco stalks.

Liquefied gaseous extenders or solvents can also be used. Particularly suitable are those extenders or carriers which are gaseous at ambient temperature and under atmospheric pressure, for example aerosol propellants, such as halogenated hydrocarbons, and also butane, propane, nitrogen, carbon dioxide and pressurized air.

Suitable surfactants are, in accordance with the invention, emulsifiers and/or foam-formers, dispersants or wetting agents having ionic or nonionic properties, or mixtures of these surfactants. Examples of these are salts of polyacrylic acid, salts of lignosulphonic acid, salts of phenolsuiphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the active compounds and/or one of the inert carriers is insoluble in water and when the application takes place in water.

As further auxiliaries, the formulations and the use forms derived therefrom may comprise dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present. Foam-formers or antifoams may also be present.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Other possible auxiliaries are mineral and vegetable oils.

If appropriate, the formulations and the use forms derived therefrom may also comprise further auxiliaries. Examples of such additives include fragrances, protective colloids, binders, adhesives, thickeners, thixotropic agents, penetrants, retention promoters, stabilizers, sequestrants and complexing agents. In general, the active compounds can be combined with any solid or liquid additive customarily used for formulation purposes.

The formulations preferably comprise between 0.00000001% and 98% by weight of active compound or, with particular preference, between 0.01% and 95% by weight of active compound, more preferably between 0.5% and 90% by weight of active compound, based on the weight of the formulation. In the above context the term "active compound" also includes active compound combinations.

The active compound combination according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers, semiochemicals or else agents for improving plant properties.

When used as an insecticide, the active compound combination according to the invention can furthermore be present in its formulations and in the use forms, prepared from these formulations, as a mixture with synergists. Synergists are compounds which increase the action of the active compounds, without it being necessary for the synergist added to be active itself.

When used as insecticide, the active compound combination according to the invention can furthermore be present in its commercially available formulations and in the use forms, prepared from these formulations, as a mixture with inhibitors which reduce degradation of the active compound after use in the environment of the plant, on the surface of parts of plants or in plant tissues.

The active compound content of the use forms (crop protection compositions) prepared from the formulations can vary within wide limits. The active compound concentration of the use forms may typically be between 0.00000001% and 95% by weight of active compound, preferably between 0.00001% and 1% by weight, based on the weight of the use form.

The compounds are employed in a customary manner appropriate for the use forms.

According to the invention, it is possible to treat all plants and plant parts with or without infestation (preventative and curative, contact or stomach insecticide). It is also possible to treat the habitat, preferably the soil, surrounding the plant. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruitbodies, fruits and seeds and also roots, tubers and rhizomes. The plant parts also include harvested material and also vegetative and generative propagation material, for example fruits, seeds, cuttings, tubers, rhizomes, slips, seed, bulbils, layers and runners.

Treatment according to the invention of the plants and plant parts with the active compound combinations is carried out directly or by allowing the compounds to act on the surroundings, environment or storage space by the customary treatment methods, for example by immersion, spraying, watering, incorporation, evaporation, fogging, scattering, painting on, injection and, in the case of propagation material, in particular in the case of seeds, also by applying one or more coats.

Plants which can be treated in accordance with the invention are in particular selected from those mentioned below.

Annual crops such as, for example: vegetables such as fruit vegetables and flower-heads/curds (for example bell peppers, chilli peppers, tomatoes, aubergines, cucumbers, cucurbits, courgettes, broad beans, runner beans, bush beans, peas, artichokes), leafy vegetables (for example lettuce, chicory, endives, cress, rocket salad, field salad, iceberg lettuce, leek, spinach, Swiss chard), tuber vegetables, root vegetables and stem vegetables (for example celeriac, beetroot, carrots, garden radish, horseradish, scorzonera, asparagus, table beet, palm shoots, bamboo shoots, moreover bulb vegetables, for example onions, leek, fennel, garlic), *brassica* vegetables (for example cauliflowers, broccoli, kohlrabi, red cabbage, white cabbage, green cabbage, Savoy cabbage, Brussels sprouts, Chinese cabbage), ornamentals, such as cut flowers (for example roses, carnations, gerbera, lilies, marguerites, chrysanthemums, tulips, daffodils, anemones, poppies, amaryllis, dahlias, azaleas, mallows, sunflowers), bedding plants, potted plants and shrubs (for example tagetes, pansies, busy lizzies, begonias), melons and maize.

Perennial crops such as, for example, citrus fruit (for example oranges, grapefruit, mandarins, lemons, limes, bitter oranges, cumquats, satsumas), pome fruit (for example apples, pears and quince), stone fruit (for example peaches, nectarines, cherries, plums, common plums, apricots), grapevines, hops, olives, tea and tropical crops, such as, for example, mangoes, papayas, figs, pineapples, dates, bananas, durians, kakies, coconuts, cacao, coffee, avocados, litchis, maracujas, guavas, almonds and nuts, such as, for example, hazelnuts, walnuts, pistachios, cashew nuts, brazil nuts, pecan nuts, butter nuts, chestnuts, hickory nuts, macadamia nuts, peanuts, soft fruit (for example blackcurrants, gooseberries, raspberries, blackberries, blueberries, strawberries, red bilberries, kiwis, cranberries), ornamentals, such as cut flowers (for example roses, carnations, gerbera, lilies, marguerites, chrysanthemums, tulips, daffodils, anemones, poppies, amaryllis, dahlias, azaleas, mallows), bedding plants, potted plants and shrubs (for example roses, tagetes, pansies, geraniums, fuchsias, hibiscus, chrysanthemums, busy lizzies, cyclamen, African violets, sunflowers, begonias), bushes and conifers (for example fig trees, rhododendron, spruce trees, fir trees, pine trees, yew trees, juniper trees, stone pines, oleanders), herbs and spices (for example aniseed, chilli pepper, bell pepper, pepper, vanilla, marjoram, thyme, cloves, juniper berries, cinnamon, tarragon, coriander, saffron, ginger).

Preference according to the invention is given to ornamental plants such as, for example, roses, geraniums, fuchsias, marguerites, bedding plants, potted plants, medicinal plants and spices such as, for example, sage, parsley, basil, coneflower, laburnum, *Salix daphnoides*, bittersweet nightshade and perennial plants such as, for example, phlox, aconitum, anemones, vegetables including fruit vegetables, tuber vegetables, root vegetables and stem vegetables, leaf vegetables and shoot vegetables, cabbage vegetables and also legumes, and perennial crops such as citrus fruit, pome fruit such as apples and pears, stone fruit such as cherries, gravevines, hops, olives, tea and tropical crops, artichokes, tobacco, peppermint, kalanchoe and dracocephalum. Particular preference is given to ornamental plants in house and garden, and also to pome fruit and stone fruit.

The active compound combinations according to the invention are also suitable for the treatment of seed. Here, particular mention may be made of the combinations according to the invention mentioned above as preferred or particularly preferred. Thus, most of the damage to crop plants which is caused by pests occurs as early as when the seed is infested during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection products after sowing or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection products being employed.

The present invention therefore in particular also relates to a method for the protection of seed and germinating plants, from attack by pests, by treating the seed with an active compound combination according to the invention. The method according to the invention for protecting seed and germinating plants against attack by pests comprises a method where the seed is treated simultaneously with an active compound of the formula (I-1), (I-2) or (I-3) and azadirachtin. It also comprises a method where the seed is treated at different points in time with an active compound of the formula (I-1), (I-2) or (I-3) and azadirachtin. The invention likewise relates to the use of the active compound combinations according to the invention for the treatment of seed for protecting the seed and the resulting plant from pests. Furthermore, the invention relates to seed which has been treated with an active compound combination according to the invention so as to afford protection from pests. The invention also relates to seed which was treated simultaneously with an active compound of the formula (I-1), (I-2) or (I-3) and azadirachtin. The invention also relates to seed which was treated at different points in time with an active compound of the formula (I-1), (I-2) or (I-3) and azadirachtin. In the case of seed which was treated at different points in time with an active compound of the formula (I-1), (I-2) or (I-3) and azadirachtin, the individual active compounds of the composition according to the invention may be present on the seed in different layers. Here, the layers comprising an active compound of the formula (I-1), (I-2) or (I-3) and azadirachtin may optionally be separated by an intermediate layer. The invention also relates to seed where an active compound of the formula (I-1), (I-2) or (I-3) and azadirachtin have been applied as component of a coating or as a further layer or further layers in addition to a coating.

One of the advantages of the present invention is that the particular systemic properties of some of the active compound combinations according to the invention mean that treatment of the seed with these active compound combinations not only protects the seed itself, but also the resulting plants after emergence, from pests. In this manner, the immediate treatment of the crop at the time of sowing or shortly thereafter can be dispensed with.

A further advantage is the synergistically increased insecticidal activity of the active compound combinations according to the invention in comparison with the individual insecticidally active compound, which exceeds the expected activity of the two active compounds when applied individually. Also advantageous is the synergistic enhancement of the fungicidal activity of the active compound combinations according to the invention compared with the individual fungicidally active compound, which exceeds the expected activity of the active compound applied individually. This makes possible an optimization of the amount of active compound employed.

Furthermore, it must be considered as advantageous that the active compound combinations according to the invention can also be employed in particular in transgenic seed, the plants arising from this seed being capable of expressing a protein directed against pests. By treating such seed with the active compound combinations according to the invention, certain pests can be controlled merely by the expression of the, for example, insecticidal protein, and additionally damage to the seed may be averted by the active compound combinations according to the invention.

The active compound combinations according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, millet, wheat, barley, oats, rye, sunflower, tobacco, potatoes or vegetables (for example tomatoes, cabbage species). The active compound combinations according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with an active compound combination according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

Within the context of the present invention, the active compound combination according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the active compound combination according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. Nos. 4,272, 417 A, 4,245,432 A, 4,808,430 A, 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples which may be mentioned are the colorants known by the names Rhodamin B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of crop protection agents and pesticides], vol. 2, Springer Verlag, 1970, p. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, such as, for example, antisense or cosuppression technology, RNA interference—RNAi—technology, if appropriate in combination with conventional methods (Genetically Modified Organisms), and parts thereof are treated. The terms "parts" or "parts of plants" or "plant parts" have been explained above.

Particularly preferably, plants of the plant cultivars which are in each case commercially available or in use are treated according to the invention. Plant cultivars are to be understood as meaning plants having new properties ("traits") and which have been generated by conventional breeding, by mutagenesis or by recombinant DNA techniques. They can be cultivars, biotypes or genotypes.

Depending on the plant species or plant cultivars, their location and growth conditions (soils, climate, vegetation period, nutrition), the treatment according to the invention may also result in superadditive ("synergistic") effects. Thus possible are, for example, reduced application rates and/or a widening of the activity spectrum and/or an increase of the activity of the compounds and compositions usable according to the invention, better plant growth, increased tolerance to high or low temperatures, increased tolerance to drought or to water or soil salt content, increased flowering, easier harvesting, accelerated maturation, higher harvest yields, higher quality and/or higher nutritional value of the harvested products, increased storability and/or processability of the harvested products, which exceed the effects normally to be expected.

The preferred transgenic plants or plant cultivars (i.e. those obtained by genetic engineering) which are to be treated according to the invention include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering, easier harvesting, accelerated maturation, higher harvest yields, higher quality and/or a higher nutritional value of the harvested products, better storability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other types of vegetable, cotton, tobacco, oilseed rape and also fruit plants (with the fruits apples, pears, citrus fruits and grapes), with particular emphasis being given to maize, soya beans, potatoes, cotton, tobacco and oilseed rape. Traits that are emphasized in particular are increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and also resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance against glyphosate, for example maize, cotton, soya beans), Liberty Link® (tolerance against phosphinothricin, for example oilseed rape), IMI® (tolerance against imidazolinones) and STS® (tolerance against sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The active compound combinations according to the invention can also be used for treating insects present in turfgrasses. Insects to be controlled which may be mentioned are, for example: Lepidoptera such as sodworms (*Crambus sperryellus* or *bonifatellus*) or, for example, *Pseudaletia unipuncta, Feltia subterrane, Peridroma saucia, Agrotis ipsilon, Hylephi phylaeus, Nomophila noctuella*, beetles (Coleoptera) (for example *Listroderes costirostris obliquus* or the flea beetle *Chaetocnema repens*) and also adults and larvae of the Scarabaeidae (*Phyllopertha horticola*, garden chafer, *Amphimallon solstitiale*, summer chafer, *Melolantha melolantha*, cockchafer, *Popillia japonica*, Japanese beetle, *Cyclocephala* spp., masked chafer, molluscs (slugs and snails), leafhoppers such as *Draeculacephala minerva* or *Deltacephalus sonorus*, leaf bugs (*Blissus insularis* Barber) and plant bugs (family Miridae, for example *Spanogonicus albofasciatus*, Diptera (for example *Oscinella frit*), scale insects (for example *Odonaspis ruthae, Antoninia graminis*), spider mites such as *Bryobia praetiosa* (clover mite) or *Aceria neocynodonis* (Bermudagrass mite) and weevils such as *Sphenophorus phoeniciensis* Chitt. or *S. venatus vestitus*.

Examples of cool-season turfgrasses are bluegrasses (*Poa* spp,), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. rubra), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) Part.) and crested dog's-tail (*Cynosurus cristatus* L.).

Examples of warm-season turfgrasses are Bermudagrass (*Cynodon* spp. L. C. Rich), zoysiagrass (*Zoysia* spp. Willd.), St. Augustine grass (*Stenotaphrum secundatum* Walt Kuntze), centipedegrass (*Eremochloa ophiuroides* Munro Hack.), carpetgrass (*Axonopus affinis* Chase), Bahia grass (*Paspalum notatum* Flugge), Kikuyugrass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Preference is generally given to cool-season turfgrasses. Especially preferred are bluegrass, bentgrass and redtop, fescues and ryegrasses. Bentgrass is especially preferred.

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The good insecticidal and acaricidal action of the active compound combinations according to the invention can be seen from the examples which follow. While the individual active compounds show weaknesses in their action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated as follows, using the formula of S. R. Colby, Weeds 15 (1967), 20-22:

If

X is the kill rate, expressed as % of the untreated control, when employing active compound A at an application rate of m g/ha or in a concentration of m ppm, Y is the kill rate, expressed as % of the untreated control, when employing active compound B at an application rate of n g/ha or in a concentration of n ppm and E is the kill rate, expressed as % of the untreated control, when employing active compounds A and B at application rates of m and n g/ha or in a concentration of m and n ppm, then $$E = X + Y - \frac{X \cdot Y}{100}$$

If the actual insecticidal or acaricidal kill rate exceeds the calculated value, the kill of the combination is superadditive, i.e. a synergistic effect is present. In this case, the actually observed kill rate must exceed the value calculated using the above formula for the expected kill rate (E).

EXAMPLE 1

Example 1 describes the effect of the combination according to the invention on caterpillars of the owlet moth (*Spodoptera exigua*) on carnations (*Dianthus caryophyllus*). Azadirachtin was employed as NeemAzal® from Trifolio GmbH. The test was carried out according to EPPO guidelines PP 1/152 (2), PP 1/181 (3), PP 1/135 (3) and PP 1/210 (1) with 4 repetitions of in each case 10 plants. At the start of the infection, the plants were treated as follows:

1. untreated
2. compound (I-1) as SL 200 (17% strength), 150 g of active compound/ha
3. azadirachtin 30 g of active compound/ha
4. compound (I-1) as SL 200+azadirachtin, 150+30 g of active compound/ha
5. positive control: imidacloprid 100 g of active compound/ha The spray solution was prepared by mixing commercial formulations and using water to adjust to the concentration mentioned. The application rate was 1000 l/ha. 3 Applications were carried out at intervals of 10-14 days. The feeding damage caused by the caterpillars on the carnation leaves was scored at weekly intervals. The results are summarized in Table 1.

TABLE 1

Efficacy of the insecticidal treatment against *Spodoptera exigua* with respect to feeding damage on carnations

| Test substance | Day 7 reduction of feeding damage in % | Day 25 reduction of feeding damage in % | Day 32 reduction of feeding damage in % | Day 40 reduction of feeding damage in % |
|---|---|---|---|---|
| untreated | 0 | 0 | 0 | 0 |
| (I-1) | 0 | 0 | 49 | 88 |
| azadirachtin | 0 | 0 | 92 | 100 |
| (I-1) + azadirachtin | 0 | 100 | 100 | 100 |
| imidacloprid | 0 | 100 | 97 | 100 |

From the table, it is evident that the active compounds azadirachtin and compound (I-1) on their own have not yet developed any activity on day 25. Here, the activity sets in only on day 32. However, for the mixture of azadirachtin and compound (I-1), 100% activity is evident as early as day 25. This test illustrates the accelerated action of the mixture compared to the individual active compounds.

EXAMPLE 2

Watering Test with Beetle Larvae

Beetle larvae (grubs) are important lawn pests. On the one hand, they feed on grass roots, damaging them directly, on the other hand they are a favoured food for birds which, searching for grubs, destroy the turf. For treatment against grubs, infested lawns are usually watered with insecticidal compositions. This type of treatment is emulated in the laboratory by Example 2.

To prepare a suitable active compound preparation, a commercial formulation of active compound or active compound combination is mixed with water until the desired concentration is reached. Pots with soil substrate were watered with the following active compound preparations:

1. untreated
2. compound (I-1) as SL 200, 600 g of active compound/ha
3. azadirachtin, 60 g of active compound/ha
4. compound (I-1) as SL 200+azadirachtin, 600+60 g of active compound/ha
5. positive control: trichlorfon 4529 g of active compound/ha L3 larvae of *Cyclocephala immaculata* were placed onto the pots. After 1, 4, 7, 14 days, the survival rate was determined, and this was used to calculate the efficacy of the compositions. 100% means that all grubs were killed, 0% means no activity. The results are summarized in Table 2.

TABLE 2

Efficacy of insecticidal treatment by watering on *Cyclocephala immaculata*

| Test substance | Effect on day 1 in % | Effect on day 4 in % | Effect on day 7 in % | Effect on day 14 in % |
|---|---|---|---|---|
| (I-1) | 0 | 28 | 0 | 29 |
| azadirachtin | 0 | 0 | 0 | 7 |
| (I-1) + azadirachtin measured | 0 | 39 | 43 | 57 |
| (I-1) + azadirachtin calculated | 0 | 28 | 0 | 34 |
| trichlorfon | 0 | 17 | 29 | 50 |

It is evident from Table 2 that for the entire duration of the test the active compound azadirachtin had no effect on grubs. For days 4, 7 and 14, a clear synergistic effect can be observed. This test illustrates the broadening of the activity spectrum of the mixture compared to the individual active compounds.

EXAMPLE 3

Phaedon cochleariae Larvae Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by spraying with the active compound preparation of the desired concentration and populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The kill rates determined are entered into Colby's formula.

In this test, the following active compound combination in accordance with the present application shows a synergistically enhanced activity compared to the active compounds applied individually:

TABLE 3

*Phaedon cochleariae* larvae test

| Active compound | Concentration | Kill in % after $1^d$ | |
|---|---|---|---|
| | | found* | calc.** |
| (I-1) | 120 g of ai/ha | 15 | |
| *Azadirachta indica* | 20% | 0 | |
| (I-1) + *Azadirachta indica* according to the invention | 120 g + 20% | 35 | 15 |

*found = activity found
**calc. = activity calculated using the Colby formula

EXAMPLE 4

*Diabrotica balteata* Test, Larvae in Soil (DIABBA)

Solvent: 4 parts by weight of acetone
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

The active compound preparation was mixed with soil. The stated concentration refers to the amount of active compound per volume unit of soil (mg/l=ppm). The treated soil is filled into pots, and 5 maize corns are placed into each pot. 3 days after sowing, larvae of the corn rootworm (*Diabrotica balteata*) are placed into the treated soil.

After the desired period of time, the kill in % is determined. The efficacy is calculated from the number of maize plants that have emerged.

In this test, the following active compound combination in accordance with the present application shows a synergistically enhanced activity compared to the active compounds applied individually:

TABLE 4

*Diabrotica balteata* larvae test

| Active compound | Concentration | Kill in % after $5^d$ | |
|---|---|---|---|
| | | found* | calc.** |
| (I-1) | 60 g of ai/ha | 75 | |
| *Azadirachta indica* | 20% | 0 | |
| (I-1) + *Azadirachta indica* according to the invention | 60 g + 20% | 100 | 75 |

*found = activity found
**calc. = activity calculated using the Colby formula

EXAMPLE 5

Example 5 describes the effect of the combination according to the invention against whiteflies (*Trialeurodes vaporariorum*) on tomatoes (*Lycopersicon esculentum*). The test was carried out under GEP according to EPPO guideline PP 1/36 (2) with 3 repetitions of in each case 4 plants. At the start of the infection, the plants were treated as follows:

1. untreated
2. compound (I-1) as SL 200 (compound according to formula (I-1), 17% strength), 50 g of active compound/ha
3. azadirachtin 30 g of active compound/ha, NeemAzal®
4. azadirachtin 15 g of active compound/ha, NeemAzal®
5. azadirachtin 5 g of active compound/ha, NeemAzal®
6. compound (I-1) as SL 200+azadirachtin, 50+30 g of active compound/ha
7. compound (I-1) as SL 200+azadirachtin, 50+15 g of active compound/ha
8. compound (I-1) as SL 200+azadirachtin, 50+5 g of active compound/ha
9. positive control imidacloprid 100 g of active compound/ha The spray solution was prepared by mixing commercial formulations and using water to adjust to the concentration mentioned. The application rate was 1000 l/ha. 2 applications were carried out at intervals of 14 days. The number of adult flies and the number of larvae were scored on days 2 to 21 after the first application. The results are summarized in Table 5. What is shown is the effect of the products, which becomes evident in a reduction of the number of insects or larvae compared to the untreated control. Imidacloprid was also tested, as positive control.

For adult whiteflies, the results show a better measured effect of the combination I-1+azadirachtin compared to the effect which can be calculated from the individual values. This synergy is particularly pronounced during the first days after the treatment. On day 2 and day 7, an improved effect was found for all azadirachtin concentrations. For 15 and 5 g of azadirachtin/ha, this synergy was also found on day 14.

In general, the onset of action against whitefly larvae is later since the active compounds have to be ingested by the animals first. On all days observed (day 7, 14, 21) and for all azadirachtin concentrations (30, 15, 5 g/ha), a marked synergistic effect was evident. Only the combination of the two active compounds I-1 and azadirachtin results in an effectiveness which allows control of whiteflies and exceeds the effectiveness of the control imidacloprid.

TABLE 5

Effectiveness of insecticidal treatment against *Trialeurodes vaporariorum* on tomatoes
Table 5: Effectiveness of insecticidal treatment against *Trialeurodes vaporariorum* on tomatoes

| Test substance | Concentration [g/ha] | Activity against adults [%] | | | | Activity against larvae [%] | | | |
|---|---|---|---|---|---|---|---|---|---|
| | | Day 2 | Day 7 | Day 14 | Day 21 | Day 2 | Day 7 | Day 14 | Day 21 |
| (I-1) | 50 | 73 | 75 | 22 | 57 | 0 | 18 | 0 | 14 |
| azadirachtin | 30 | 45 | 47 | 32 | 56 | 0 | 2 | 13 | 0 |
| azadirachtin | 15 | 47 | 54 | 49 | 80 | 0 | 13 | 37 | 0 |
| azadirachtin | 5 | 23 | 7 | 0 | 16 | 0 | 24 | 12 | 0 |
| (I-1) + azadirachtin measured | 50 + 30 | 94 | 93 | 41 | 87 | 0 | 63 | 71 | 45 |
| (I-1) + azadirachtin calculated | 50 + 30 | 83 | 87 | 46 | 90 | 0 | 20 | 13 | 14 |
| (I-1) + azadirachtin measured | 50 + 15 | 96 | 98 | 79 | 97 | 0 | 67 | 79 | 41 |
| (I-1) + azadirachtin calculated | 50 + 15 | 85 | 89 | 60 | 91 | 0 | 29 | 37 | 14 |
| (I-1) + azadirachtin measured | 50 + 5 | 85 | 89 | 62 | 30 | 0 | 51 | 29 | 89 |
| (I-1) + azadirachtin calculated | 50 + 5 | 79 | 77 | 22 | 63 | 0 | 38 | 12 | 14 |
| imidacloprid | 100 | 51 | 89 | 68 | 65 | 0 | 60 | 50 | 52 |

EXAMPLE 6

This example describes a further test with the formulation according to the invention against whiteflies (*Trialeurodes vaporariorum*) on tomatoes (*Lycopersicon esculentum*). The test was carried out under GEP according to EPPO guideline PP 1/36(2) with 4 repetitions of in each case 5 plants. At the start of the infection, the plants were treated as follows:
1. untreated
2. compound (I-1) as SL 200 (compound according to formula (I-1), 17% strength), 50 g of active compound/ha
3. azadirachtin 15 g of active compound/ha, NeemAzal®
4. azadirachtin 5 g of active compound/ha, NeemAzal®
5. compound (I-1) as SL 200+azadirachtin, 50+15 g of active compound/ha
6. compound (I-1) as SL 200+azadirachtin, 50+5 g of active compound/ha
7. positive control imidacloprid 100 g of active compound/ha The spray solution was prepared by mixing commercial formulations and using water to adjust to the concentration mentioned. The application rate was 1000 l/ha. 2 applications were carried out at intervals of 10 days. The number of adult flies and the number of larvae were scored on days 2 to 32 after the first application. The results are summarized in Table 6. What is shown is the effect of the products, which becomes evident in a reduction of the number of insects or larvae compared to the untreated control. Imidacloprid was also tested, as positive control.

In particular in the action against whitefly larvae, the reduction of animal numbers due to the active compound occurred much earlier than in a treatment with the individual compounds. For the individual compounds, a reduction of the larvae was noticeable only on day 14, whereas the effect of the combination according to the invention was evident even on day 2 and day 7. Furthermore, on days 14 and 21 the effect of the combination was much more pronounced. Thus, the combination according to the invention has a great advantage over the individual combinations and is essential for an effective control of whiteflies.

TABLE 6

Effectiveness of insecticidal treatment against *Trialeurodes vaporariorum* on tomatoes
Table 6: Effectiveness of insecticidal treatment against *Trialeurodes vaporariorum* on tomatoes

| Test substance | Concentration [g/ha] | Activity against adults [%] | | | | | Activity against larvae [%] | | | | |
|---|---|---|---|---|---|---|---|---|---|---|---|
| | | Day 2 | Day 7 | Day 14 | Day 21 | Days 28-32 | Day 2 | Day 7 | Day 14 | Day 21 | Days 28-32 |
| (I-1) | 50 | 86 | 88 | 93 | 96 | 67 | 0 | 0 | 18 | 4 | 68 |
| azadirachtin | 15 | 57 | 64 | 65 | 76 | 76 | 0 | 0 | 20 | 32 | 37 |
| azadirachtin | 5 | 41 | 41 | 40 | 47 | 40 | 0 | 0 | 0 | 0 | 0 |
| (I-1) + azadirachtin measured | 50 + 15 | 99 | 100 | 100 | 100 | 88 | 21 | 39 | 65 | 66 | 96 |

TABLE 6-continued

Effectiveness of insecticidal treatment against *Trialeurodes vaporariorum* on tomatoes
Table 6: Effectiveness of insecticidal treatment against *Trialeurodes vaporariorum* on tomatoes

| Test substance | Concentration [g/ha] | Activity against adults [%] | | | | | Activity against larvae [%] | | | | |
|---|---|---|---|---|---|---|---|---|---|---|---|
| | | Day 2 | Day 7 | Day 14 | Day 21 | Days 28-32 | Day 2 | Day 7 | Day 14 | Day 21 | Days 28-32 |
| (I-1) + azadirachtin calculated | 50 + 15 | 94 | 96 | 98 | 100 | 92 | 0 | 0 | 34 | 35 | 79 |
| (I-1) + azadirachtin measured | 50 + 5 | 96 | 100 | 99 | 80 | 80 | 24 | 35 | 38 | 93 | 92 |
| (I-1) + azadirachtin calculated | 50 + 5 | 92 | 93 | 99 | 98 | 80 | 0 | 0 | 18 | 4 | 68 |
| imidacloprid | 100 | 91 | 96 | 98 | 99 | 91 | 0 | 57 | 70 | 68 | 94 |

EXAMPLE 7

Example 7 describes the effect of the combination according to the invention on the greenhouse red spider mite (*Tetranychus urticae*) on roses. The test was carried out in a greenhouse under GEP according to EPPO guideline PP 1/168(2) with 4 repetitions of in each case 4 plants. At the start of the infection, the plants were treated as follows:
1. untreated
2. compound (I-1) as SL 200 (compound according to formula (I-1), 17% strength), 50 g of active compound/ha
3. azadirachtin 30 g of active compound/ha, NeemAzal®
4. azadirachtin 5 g of active compound/ha, NeemAzal®
5. compound (I-1) as SL 200+azadirachtin, 50+30 g of active compound/ha
6. compound (I-1) as SL 200+azadirachtin, 50+5 g of active compound/ha
7. positive control imidacloprid 100 g of active compound/ha The spray solution was prepared by mixing commercial formulations and using water to adjust to the concentration mentioned. The application rate was 1000 l/ha. 2 applications were carried out at intervals of 14 days. The number of spider mites on days 2 to 32 after the first application was scored. The results are summarized in Table 7. What is shown is the effect of the products, which becomes evident in a reduction of the number of spider mites compared to the untreated control.

TABLE 7

Effectiveness of the insecticidal treatment against spider mites on roses
Table 7: Effectiveness of the insecticidal treatment against spider mites on roses

| Test substance | Concentration [g/ha] | Activity against *Tetranychus urticae* [%] | | | | |
|---|---|---|---|---|---|---|
| | | Day 2 | Day 7 | Day 14 | Day 21 | Days 28-32 |
| (I-1) | 50 | 28 | 15 | 43 | 12 | 15 |
| azadirachtin | 30 | 21 | 16 | 20 | 7 | 0 |
| azadirachtin | 5 | 30 | 0 | 10 | 19 | 6 |
| (I-1) + azadirachtin measured | 50 + 30 | 23 | 37 | 39 | 56 | 36 |
| (I-1) + azadirachtin calculated | 50 + 30 | 39 | 29 | 50 | 18 | 15 |
| (I-1) + azadirachtin measured | 50 + 5 | 26 | 31 | 42 | 56 | 56 |
| (I-1) + azadirachtin calculated | 50 + 5 | 50 | 15 | 49 | 29 | 20 |
| imidacloprid | 100 | 20 | 16 | 11 | 27 | 46 |

The results show a better measured effect of the combination I-1+azadirachtin compared to the effect which can be calculated from the individual values. This synergy is evident on days 7, 21 and 28-32 after the first treatment. The improved activity was observed at 30 and 5 g of azadirachtin/ha.

EXAMPLE 8

Example 8 describes the effect of the combination according to the invention on fall armyworm caterpillars (*Spodoptera exigua*) on maize (*Zea mays*). The test was carried out in a greenhouse under GEP with 2 repetitions of in each case 8 plants. After uniform infection, the plants were treated as follows:
1. untreated
2. compound (I-1) as SL 200 (compound according to formula (I-1), 17% strength), 50 g of active compound/ha
3. azadirachtin 30 g of active compound/ha, NeemAzal®
4. azadirachtin 5 g of active compound/ha, NeemAzal®
5. compound (I-1) as SL 200+azadirachtin, 50+30 g of active compound/ha
6. compound (I-1) as SL 200+azadirachtin, 50+5 g of active compound/ha
7. positive control imidacloprid 100 g of active compound/ha The spray solution was prepared by mixing commercial formulations and using water to adjust to the concentration mentioned. The application rate was 1000 l/ha. 2 applications were carried out at intervals of 11 days. The feeding damage by the caterpillars on the maize on days 7 to 42 after the first application was scored. The results are summarized in Table 8. What is shown is the effect of the products, which becomes evident in a reduction of feeding damage compared to the untreated control.

TABLE 8

Effectiveness of the insecticidal treatment against fall armyworm caterpillars on maize
Table 8: Effectiveness of the insecticidal treatment against fall armyworm caterpillars on maize

| Test substance | Concentration [g/ha] | Activity against *Spodoptera frugiperda* [%] | | | | |
|---|---|---|---|---|---|---|
| | | Day 7 | Day 14 | Day 21 | Days 28-32 | Days 35-42 |
| (I-1) | 50 | 0 | 0 | 0 | 0 | 0 |
| azadirachtin | 30 | 0 | 7 | 53 | 84 | 80 |
| azadirachtin | 5 | 0 | 29 | 61 | 77 | 81 |
| (I-1) + azadirachtin measured | 50 + 30 | 0 | 49 | 66 | 83 | 85 |
| (I-1) + azadirachtin calculated | 50 + 30 | 0 | 7 | 53 | 84 | 80 |
| (I-1) + azadirachtin measured | 50 + 5 | 0 | 53 | 62 | 80 | 84 |
| (I-1) + azadirachtin calculated | 50 + 5 | 0 | 29 | 61 | 77 | 81 |
| imidacloprid | 100 | 24 | 57 | 14 | 12 | 10 |

For the two azadirachtin concentrations examined (30 and 5 g/ha), compared to the individual active compounds, a more rapid onset of action and an improved activity against fall armyworm caterpillars was observed for the combination of the active compounds I-1 and azadirachtin.

EXAMPLE 9

Bioassay

Example 9 also describes the effect of the combination according to the invention on caterpillars of diamondback moth *Plutella xylostella* on Savoy cabbage. The plants were grown in a greenhouse, and five plants each were treated as follows: The spray solution was prepared by mixing commercial formulations and using water to adjust to the concentration mentioned. The application rate was 1000 l/ha.
1. untreated
2. compound (I-1) as SL 200 (compound according to formula (I-1), 17% strength), 50 g of active compound/ha
3. azadirachtin 30 g of active compound/ha, NeemAzal®
4. azadirachtin 15 g of active compound/ha, NeemAzal®
5. azadirachtin 5 g of active compound/ha, NeemAzal®
6. compound (I-1) as SL 200+azadirachtin, 50+30 g of active compound/ha
7. compound (I-1) as SL 200+azadirachtin, 50+15 g of active compound/ha
8. compound (I-1) as SL 200+azadirachtin, 50+5 g of active compound/ha
9. positive control imidacloprid 100 g of active compound/ha The plants were incubated under greenhouse conditions (20° C., 70% relative atmospheric humidity), the plants being placed at random. After 3 days, the first leaf samples were taken. Here, 5 leaves were picked from each plant. 10 leaf discs of a diameter of 6 cm were punched from the leaves and placed in Petri dishes covered with moistened filter paper. Once the leaf discs had been placed into the Petri dishes, 5 *Plutella xylostella* larvae of the L2 instar were added. The Petri dishes were placed on a tablett, covered with a dark film and kept at 20° C. in the laboratory. Evaluation was carried out on days 9, 14 and 21 after the addition of the larvae, the number of surviving animals being scored.

The results are summarized in Table 9. What is shown is the effect of the products, which becomes evident in a reduction of the number of diamondback moths compared to the untreated control.

Here, too, the activity of the combination according to the invention of I-1 and azadirachtin, the onset of which is about 5 days earlier, is remarkable. At the concentrations of 50 g of I-1/ha and 30 g of azadirachtin/ha, a 100% activity is reached even on day 9. At the lower concentration of 50 g of I-1/ha and 5 g of azadirachtin/ha, the activity achieved on day 9 was still almost 50%, compared to 0% activity of the individual components. On day 14, a markedly improved activity is evident for all concentrations.

TABLE 9

Effectiveness of the insecticidal treatment against diamondback moths on Savoy cabbage
Table 9: Effectiveness of the insecticidal treatment against diamondback moths on Savoy cabbage

| Test substance | Concentration [g/ha] | Activity against *Plutella xylostella* [%] | | |
|---|---|---|---|---|
| | | Day 9 | Day 14 | Day 21 |
| (I-1) | 50 | 0 | 21 | 34 |
| azadirachtin | 30 | 46 | 72 | 25 |
| azadirachtin | 15 | 18 | 31 | 38 |
| azadirachtin | 5 | 0 | 15 | 25 |
| (I-1) + azadirachtin measured | 50 + 30 | 100 | 100 | 38 |
| (I-1) + azadirachtin calculated | 50 + 30 | 46 | 78 | 51 |
| (I-1) + azadirachtin measured | 50 + 15 | 18 | 51 | 19 |
| (I-1) + azadirachtin calculated | 50 + 15 | 18 | 46 | 59 |
| (I-1) + azadirachtin measured | 50 + 5 | 46 | 67 | 34 |
| (I-1) + azadirachtin calculated | 50 + 5 | 0 | 33 | 51 |
| imidacloprid | 100 | 43 | 36 | 41 |

EXAMPLE 10

Example 10 describes the effect of the combination according to the invention on caterpillars of the turnip flea beetle *Phyllotreta nigripes* on cabbage. The test was carried out according to EPPO guidelines PP 1/210(1), PP 1/152 (2), PP 1/181 (3) and PP 1/135 with 4 repetitions of in each case 10 plants. The plants were treated as follows:
1. untreated
2. compound (I-1) as SL 200 (compound according to formula (I-1), 17% strength), 150 g of active compound/ha
3. azadirachtin 30 g of active compound/ha, NeemAzal®
4. compound (I-1) as SL 200+azadirachtin, 150+30 g of active compound/ha
5. positive control imidacloprid 100 g of active compound/ha The spray solution was prepared by mixing commercial formulations and using water to adjust to the concentration mentioned. The application rate was 1000 l/ha. 2 applications were carried out at intervals of 14 days. The number of live caterpillars on days 7 to 32 after the first application was scored. The results are summarized in Table 10. What is shown is the effect of the products, which becomes evident in a reduction of the number of caterpillars compared to the untreated control.

The results show a better measured effect of the combination I-1+azadirachtin compared to the effect which can be calculated from the individual values. This synergy is evident for all days examined at a dosage of 150 g of I-1/ha and 30 g of azadirachtin/ha.

TABLE 10

Effectiveness of the insecticidal treatment against the turnip flea beetle
Table 10: Effectiveness of the insecticidal treatment against the turnip flea beetle

| Test substance | Concentration [g/ha] | Activity against *Phyllotreta nigripes* [%] | | | |
|---|---|---|---|---|---|
| | | Day 7 | Days 14-16 | Days 21-25 | Days 28-32 |
| (I-1) | 150 | 0 | 9.5 | 7.4 | 2.8 |
| azadirachtin | 30 | 29 | 51 | 35 | 34 |
| (I-1) + azadirachtin measured | 150 + 30 | 46 | 62 | 58 | 53 |
| (I-1) + azadirachtin calculated | 150 + 30 | 29 | 56 | 40 | 36 |
| imidacloprid | 100 | 52 | 51 | 49 | 43 |

The invention claimed is;

1. A composition comprising synergistic amounts of a compound of formula (I-1)

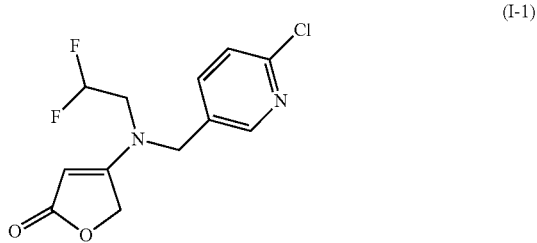 [SMILES: O=C1C=C(N(Cc2ccc(Cl)nc2)CC(F)F)CO1]

and azadirachtin, wherein the ratio of the compound of formula (I-1) to azadirachtin is from about 25:1 to about 1:25.

2. The composition according to claim 1 wherein the azadirachtin is in pure active compound form.

3. The composition according to claim 1 wherein the azadirachtin comprises a product of extraction of neem tree seeds.

4. The composition according to claim 1 further comprising azadirachtin in a formulation.

5. The composition according to claim 1 further comprising the product of neem tree seed extraction as a formulation.

6. The composition according to Claim 1 wherein said azadirachtin comprises a proportion of azadirachtin A (molecular weight 720.7 g/mol) of from 20% to 50%.

7. The composition according to claim 1 wherein the ratio of the compound of formula (I-1) to azadirachtin is from about 5:1 to about 1:5.

8. A formulation comprising the composition according to claim 1, and an auxiliary.

9. A method for controlling insects or acarids comprising applying the composition according to claim 1 to plants and plant parts with or without infestation by said insects or acarids.

10. A method for controlling insects or acarids comprising introducing the composition according to claim 1 into the habitat surrounding plants with or without infestation by said insects or acarids.

11. The method according to claim 9 wherein the plants are ornamental plants in house or garden.

12. The method according to claim 10 wherein the plants are ornamental plants in house or garden.

13. The formulation of claim 8, wherein said auxiliary is an extender, solvent, carrier and/or surfactant, 14. The composition of claim 1, wherein the ratio of the compound of formula (I-1) to azadiraehtin is from 1.7:1 to 10:1.

* * * * *